United States Patent
Karjalainen et al.

(10) Patent No.: US 11,332,460 B2
(45) Date of Patent: May 17, 2022

(54) PROCESS FOR THE PREPARATION OF A SULFONAMIDE STRUCTURED KINASE INHIBITOR

(71) Applicant: ORION CORPORATION, Espoo (FI)

(72) Inventors: Oskari Karjalainen, Helsinki (FI); Pekka Pietikäinen, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 16/953,468

(22) Filed: Nov. 20, 2020

(65) Prior Publication Data

US 2021/0139462 A1 May 13, 2021

Related U.S. Application Data

(63) Continuation of application No. 16/495,865, filed as application No. PCT/FI2018/050214 on Mar. 22, 2018, now Pat. No. 10,870,637.

(30) Foreign Application Priority Data

Mar. 23, 2017 (FI) .................................. 20175272

(51) Int. Cl.
*C07D 403/04* (2006.01)
(52) U.S. Cl.
CPC ................. *C07D 403/04* (2013.01)

(58) Field of Classification Search
CPC .................................................. C07D 403/04
See application file for complete search history.

(56) References Cited

U.S. PATENT DOCUMENTS 9,447,091 B2 * 9/2016 Linnanen ........... A61K 31/4196

FOREIGN PATENT DOCUMENTS

WO    WO 2013/053983 A1    4/2013

OTHER PUBLICATIONS

International Search Report, issued by the European Patent Office in International Application No. PCT/FI2018/050214, dated Jul. 4, 2018 (2 pages).

* cited by examiner

*Primary Examiner* — Kamal A Saeed
(74) *Attorney, Agent, or Firm* — Finnegan, Henderson, Farabow, Garrett & Dunner, LLP

(57) ABSTRACT

The present disclosure relates to an improved process for the preparation of a sulfonamide structured kinase inhibitor, namely N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (1A) and pharmaceutically acceptable salts thereof. Compound of formula (1A) is a selective inhibitor of FGFR/VEGFR kinase families and is useful in the treatment of cancer.

9 Claims, No Drawings

PROCESS FOR THE PREPARATION OF A SULFONAMIDE STRUCTURED KINASE INHIBITOR

This is a continuation of pending application Ser. No. 16/495,865, filed Sep. 20, 2019, which is a national stage filing under 35 U.S.C. § 371 of International Application No. PCT/FI2018/050214, filed Mar. 22, 2018, which claims the benefit of priority to Finnish Patent Application No. 20175272, filed Mar. 23, 2017, all of which are incorporated herein by reference.

TECHNICAL FIELD

The present invention relates to an improved process for the preparation of sulfonamide structured kinase inhibitor, namely N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (1A) and pharmaceutically acceptable salts thereof.

BACKGROUND OF THE INVENTION

The compound N-(2',4'-difluoro-5-(5-(1-methyl-H-pyrazol-4-yl)-1H-benzo[d]imidazol-1-yl)-[1,1'-biphenyl]-3-yl) cyclopropanesulfonamide of formula (1A) and derivatives thereof have been disclosed in WO 2013/053983. Compound of formula (I A) and pharmaceutically acceptable salts thereof are selective inhibitors of FGFR/VEGFR kinase families and are useful in the treatment of cancer.

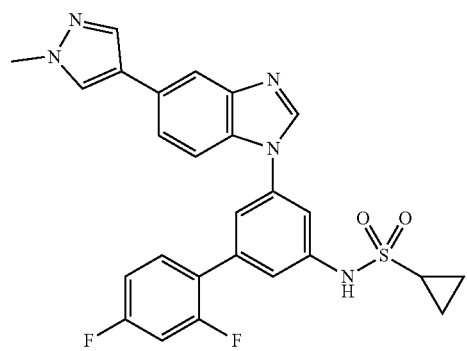

(1A)

WO 2013/053983 discloses a process for the preparation of the compound of formula (I A) according to Scheme 1:

SCHEME 1

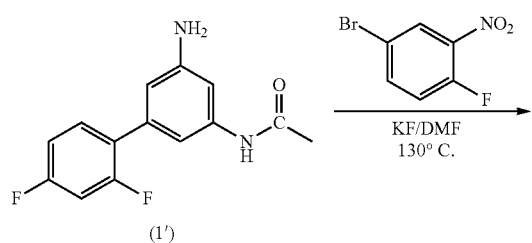

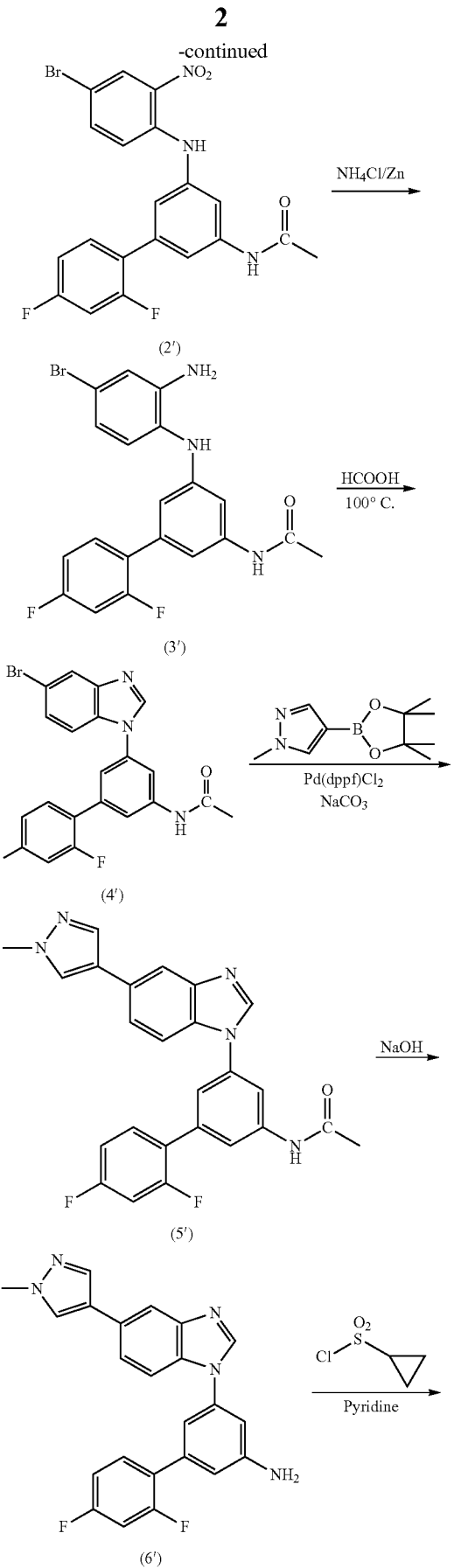

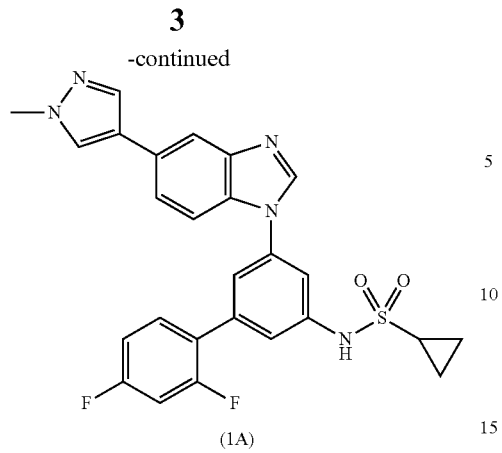

(1A)

The process of Scheme 1 has several drawbacks. The first reaction step with 4-bromo-1-fluoro-2-nitrobenzene involves harsh conditions, liberation of harmful hydrogen fluoride, necessity to purify the product by chromatography and poor yield (45%). The subsequent conversion of compound (2') to compound (4') by reduction of the nitro group with NH$_4$Cl/Zn followed by ring closure with HCOOH requires isolation of the intermediate compound (3'). Addition of 1-methyl-1H-pyrazol-4-yl ring to the compound (4') to obtain compound (5') requires large amount of expensive palladium catalyst while the yield still remains low. Also the hydrolysis reaction to compound (6) and the last step of creating a sulfonamine bond suffer from low yields.

Thus, there is a need for a more economical process that is suitable for the manufacture of the compound of formula (1A) in a large scale.

SUMMARY OF THE INVENTION

It has now been found that the compound of formula (1A) can be prepared using a process which is more practical and economical and suitable for use in a large scale. The drawbacks of the method disclosed in WO 2013/053983 can be largely avoided.

Thus the present invention provides a process for the preparation of a compound of formula (A) or a pharmaceutically acceptable salt thereof

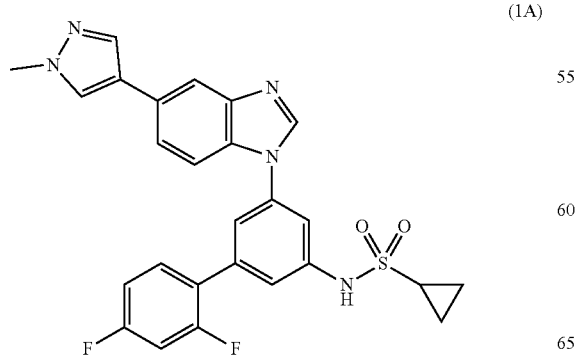

(1A)

comprising the steps of a) reacting 2',4'-difluoro-[1,1'-biphenyl]-3,5-diamine of formula (V)

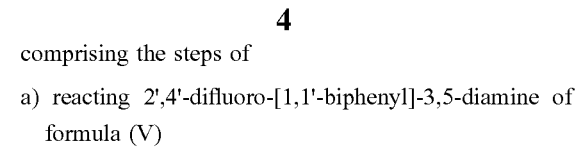

(V)

with 4-bromo-2-fluoronitrobenzene in the presence of an organic base and an organosilane, to obtain a compound of formula (IV)

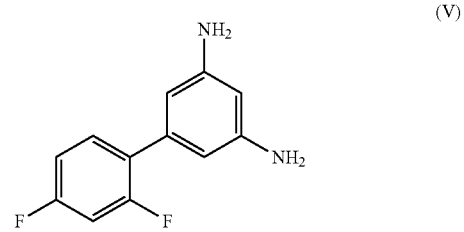

(IV)

b) treating the product obtained from step (a) with an organic acid and isolating the formed organic salt;

c) releasing the compound of formula (IV) from its salt form;

d) either (i) reacting the compound of formula (IV) with cyclo propanesulfonyl chloride to obtain a compound of formula (III)

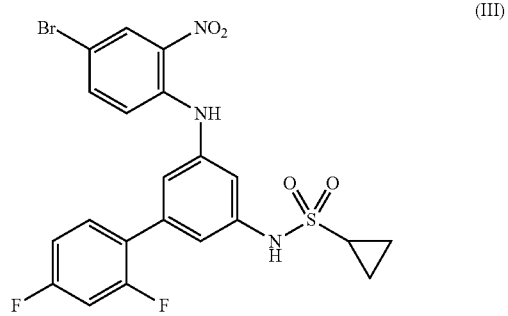 [SMILES: O=[N+]([O-])c1cc(Br)ccc1Nc1cc(NS(=O)(=O)C2CC2)cc(-c2ccc(F)cc2F)c1]

(III)

and subsequently reacting the compound of formula (III) with 1-methyl-4-(4,4,5,5-tetramethyl-1,3,2-dioxaborolan-2-yl)-1H-pyrazole;

or (ii) reacting the compound of formula (IV) with 1-methyl-4-(4,4,5,5-tetra-methyl-1,3,2-dioxaborolan-2-yl)-1H-pyrazole to obtain a compound of formula (IIIb)

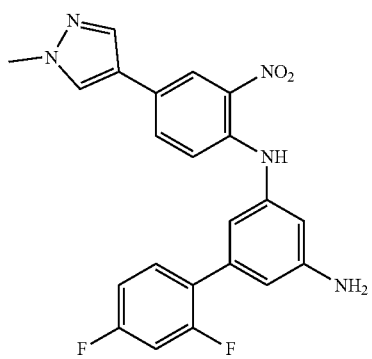

(IIIb)

and subsequently reacting the compound of formula (IIIb) with cyclopropane-sulfonyl chloride;

to obtain a compound of formula (II);

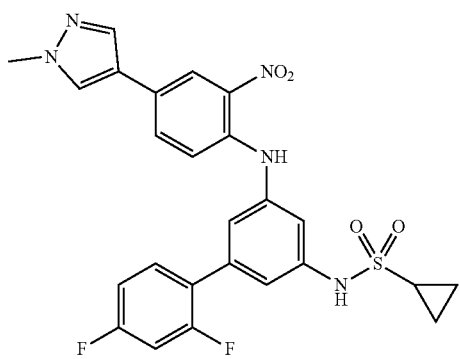

(II)

e) hydrogenating the compound of formula (II) in formic acid in the presence of a catalyst to obtain a compound of formula (1A), which is optionally converted to its pharmaceutically acceptable salt.

In another aspect, the present invention provides a process for the preparation of a compound of formula (IV)

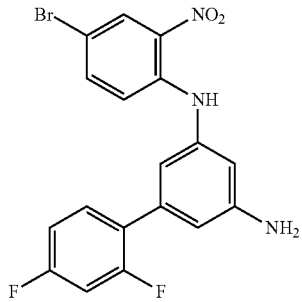

(IV)

comprising the steps of a) reacting 2',4'-difluoro-[1,1'-biphenyl]-3,5-diamine of formula (V)

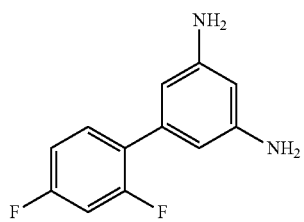

(V)

with 4-bromo-2-fluoronitrobenzene in the presence of an organic base and an organosilane to obtain a compound of formula (IV)

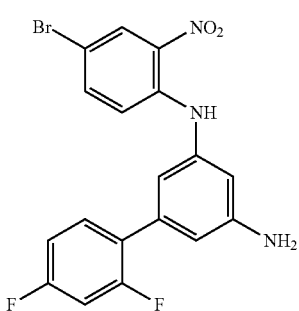

(IV)

b) treating the product obtained from step (a) with an organic acid and isolating the formed organic salt;

c) releasing the compound of formula (IV) from its salt form.

In another aspect, the present invention provides the use of the compound of formula (IV) in the preparation of the compound of formula (1A), wherein the compound of formula (IV) is prepared according to the method disclosed above.

In another aspect, the present invention provides a process for the preparation of a compound of formula (1A) or a pharmaceutically acceptable salt thereof

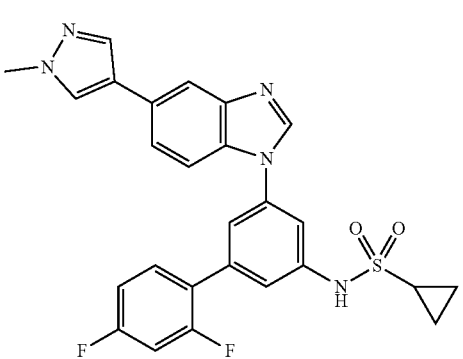

(1A)

comprising the step of hydrogenating the compound of formula (II)

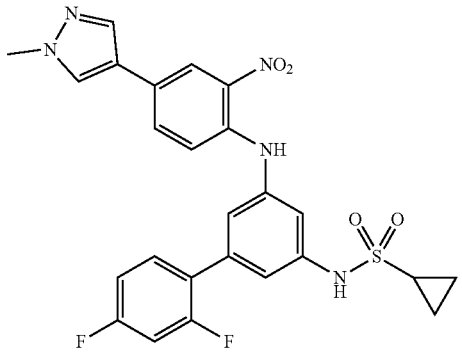

(II)

in formic acid in the presence of a catalyst to obtain a compound of formula (1A), which is optionally converted to its pharmaceutically acceptable salt.

In another aspect, the present invention provides new intermediates of formula (V), (IV), (III), (IIIb) and (II).

In another aspect, the present invention provides the use of any of intermediates of formula (V), (IV), (III), (IIIb) or (II) in the preparation of the compound of formula (1A) or a pharmaceutically acceptable salt thereof.

DETAILED DESCRIPTION OF THE INVENTION

In accordance with the present invention 2',4'-difluoro-[1,1'-biphenyl]-3,5-diamine of formula (V)

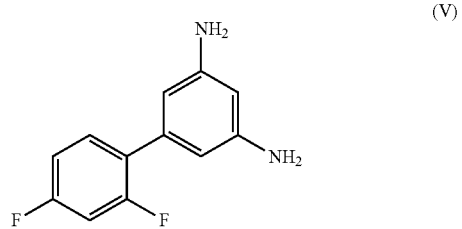 [SMILES: Nc1cc(N)cc(-c2ccc(F)cc2F)c1]

(V)

is first reacted with 4-bromo-2-fluoronitrobenzene in the presence of an organic base and an organosilane to obtain a compound of formula (IV)

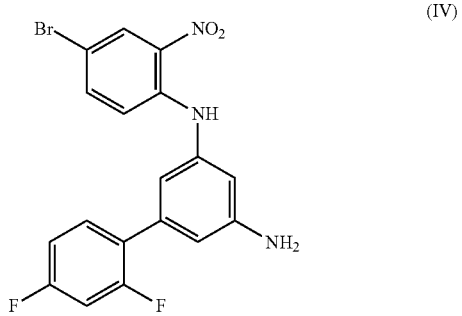 [SMILES: Nc1cc(Nc2ccc(Br)cc2[N+](=O)[O-])cc(-c2ccc(F)cc2F)c1]

(IV)

in high yield without extraction and distillation steps and without need of purification by chromatography.

The reaction is conducted at elevated temperature in a suitable solvent such as dimethyl sulfoxide. The organic base can be any suitable organic base known in the art, for example N,N-diisopropylethylamine (DIPEA). It has been found that the reaction is conveniently carried out in the presence of an organosilane compound which eliminates the harmful and highly corrosive hydrogen fluoride which is liberated in the reaction. Any suitable organosilane compound can be used ethoxytrimethylsilane being preferred. The reaction is carried out at elevated temperature such as 80-110° C., for example 90-100° C., until reaction is complete, typically for less than 8 h, for example for 5 h. The reaction mixture can then be cooled, water and methanol is suitably added, and the product is allowed to precipitate for example at 20° C. The obtained compound of formula (IV) can then be isolated for example by filtering, washing with water and methanol and drying at reduced pressure at about 60° C.

The obtained compound of formula (IV) usually contains over-reaction product which is formed when compound of formula (V) reacts twice with 4-bromo-2-fluoronitrobenzene. This over-reaction product is difficult to isolate from compound (IV) and is problematic in the next steps of the process.

It has been found that the over-reaction product can be conveniently removed by treating the compound of formula (IV) obtained from the previous with an organic acid and isolating the formed organic salt. Suitable organic salts include, for example, sulfonic acids such as methanesulfonic acid, p-toluenesulfonic acid, o-toluenesulfonic acid and ethanesulfonic acid, or benzenesulfonic acid, benzoic acid, tartaric acid, fumaric acid and the like. Preferred are methanesulfonic acid or p-toluenesulfonic acid, methanesulfonic acid being most preferred. The salt formation is carried out by dissolving compound (IV) in a suitable organic solvent, for example in the mixture of toluene and 2-butanone, by heating, for example to about 70-80° C. The organic acid, for example methanesulfonic acid, can then be added in the amount of about 1 equivalent in respect to compound (IV) followed by stirring, for example for about 30 to 60 min. The mixture is then cooled to a temperature where the organic salt of compound (IV) starts to precipitate. When methanesulfonic acid is used, the mixture is suitably cooled to about 55-65° C. The precipitated salt can then be collected, for example by filtration.

The compound (IV) can then be released from its salt form by heating the salt in a suitable organic solvent, for example in the mixture of toluene and 2-butanone, for example to about 70-80° C., and adding an organic base, such as triethylamine, to the mixture. The compound (IV) can then be precipitated by cooling the mixture for example to about 15-25° C. The precipitated compound (IV) which is now substantially free of the over-reaction product can be isolated for example by filtering, washing with 2-propanol and drying in a vacuum for example at about 60° C.

The conversion of compound (IV) into compound (II) includes addition of a 1-methyl-H-pyrazole group and a cyclopropanesulfonyl group to the structure of compound (IV). These two steps can be carried out sequentially in any order.

Accordingly, the conversion of compound of formula (IV) into compound (II) can be carried out by either (i) treating the compound of formula (IV) with cyclopropane-sulfonyl chloride to obtain a compound of formula (III)

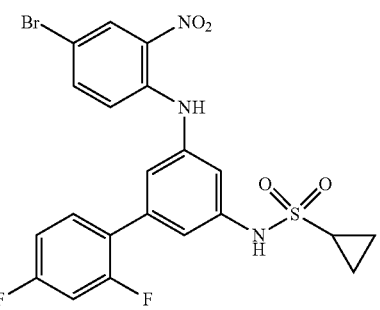

(III)

and subsequently reacting the compound of formula (III) with 1-methyl-4-(4,4,5,5-tetramethyl-1,3,2-dioxaborolan-2-yl)-1H-pyrazole;

or (ii) treating the compound of formula (IV) with 1-methyl-4-(4,4,5,5-tetra-methyl-1,3,2-dioxaborolan-2-yl)-1H-pyrazole to obtain a compound of formula (IIIb)

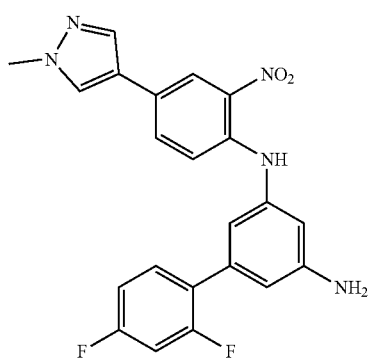

(IIIb)

and subsequently reacting the compound of formula (IIIb) with cyclopropane-sulfonyl chloride.

Compound (III) can be obtained in high yield without extraction and distillation steps and without need of purification by chromatography by treating compound (IV) with cyclopropanesulfonyl chloride in the presence of a base, conveniently pyridine which optionally may also function as solvent, optionally in a suitable solvent such as, for example, ethyl acetate at temperatures ranging from about 10° C. to about 65° C., to furnish compound (III). Compound (III) can be suitably precipitated from the reaction mixture by addition of an acid, for example acetic acid, water and ethanol or 2-propanol, heating the mixture, for example, to about 40-75° C. and then cooling, for example, to about 0-25° C. Compound (III) can be isolated, for example, by filtering, washing with water and ethanol or 2-propanol, and drying in vacuum at elevated temperature, for example at 60° C.

Compound (II) can be obtained in high yield without extraction and distillation steps and without need of purification by chromatography by treating compound (III) with 1-methyl-4-(4,4,5,5-tetramethyl-1,3,2-dioxaborolan-2-yl)-1H-pyrazole in a suitable solvent such as, for example, a mixture of water and DMSO, in the presence of a base, a catalyst and activated charcoal. Suitable bases include carbonates such as potassium carbonate, cesium carbonate and sodium carbonate, potassium carbonate being preferred. Suitable catalysts include palladium catalysts such as palladium (II) acetate which may be complexed with triphenylphosphine. Typically 0.0050-0.01 equivalents of palladium (II) acetate has found to be sufficient. The reaction mixture is preferably heated to about 90-110° C. over several hours, for example 4 hours, after which the mixture is cooled, for example to about 75-85° C., followed by addition of ethanol. The reaction mixture may then be filtered. The filtrate is cooled, for example to about 55-65° C., followed by addition of water. The mixture may then be cooled further, for example to about 0-10° C., and the precipitated compound (II) can be isolated, for example, by filtering, washing with water and ethanol, and drying in vacuum at elevated temperature, for example at 60° C.

Compound (IIIb) can be obtained by treating compound (IV) with 1-methyl-4-(4,4,5,5-tetramethyl-1,3,2-dioxaborolan-2-yl)-1H-pyrazole using the same procedure as described above for the preparation of compound (II).

Compound (II) can be obtained from compound (IIIb) by treating compound (IIIb) with cyclopropanesulfonyl chloride using the same procedure as described above for the preparation of compound (III).

Finally, compound (II) can be converted directly to a compound of formula (1A) by hydrogenating compound (II) in formic acid in the presence of a catalyst without the need to isolate the intermediate compound having nitro group reduced to amine group. Suitable catalyst includes palladium catalysts such as 5% palladium on charcoal. Compound (II), formic acid, and the catalyst are charged into the reactor inerted with nitrogen followed by introducing hydrogen gas. The reactor is heated to about 30° C. and the hydrogenation is continued until the reaction has completed. The catalyst is filtrated off and the filtrate is heated, for example to about 100° C. Some of the formic acid can be distilled off under reduced pressure. Thereafter suitably 2-propanol and water is added to the reaction mixture while keeping the temperature higher than about 70° C. Compound (1A) can be precipitated, optionally with seeding, by cooling the mixture slowly, for example during about 8-10 hours to about 0° C. Compound (IA) can be isolated, for example, by filtering, washing with 2-propanol, and drying in vacuum at elevated temperature, for example at 60° C.

The obtained compound (1A) is typically in the form of 1:1 solvate with formic acid. The formic acid can be removed from the compound (1A) for example by heating the solvate in a suitable organic solvent such as, for example, 2-butanone, methanol, ethyl acetate, toluene, methyl tert-butyl ether and dichloromethane. For example, heating the solvate in 2-butanone at about 75° C. for about 2 h followed by cooling the mixture, isolating the precipitate by filtering, washing with 2-butanone and drying in a vacuum at about 60° C. yielded compound (1A) free of formic acid.

If desired, compound (1A) may be converted to a pharmaceutically acceptable salt thereof by methods known in the art.

The starting compound (V)

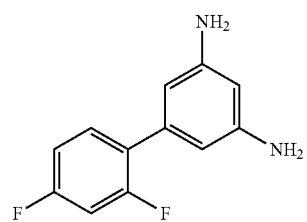

(V)

can be prepared, for example, by
a) reacting 1-bromo-3,5-dinitrobenzene of formula (VII)

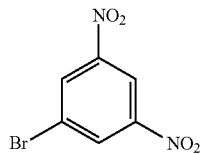
(VII)

with 2,4-difluorophenylboronic acid at elevated temperature in the presence of catalyst, e.g. palladium catalyst, and a base, e.g. trimethylamine, in a suitable solvent, e.g. acetonitrile-water solvent, to obtain 2,4-difluoro-3',5'-dinitro-1,1'-biphenyl of formula (VI)

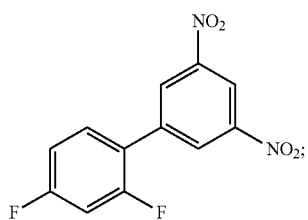
(VI)

and
b) reducing the compound of formula (VI) by hydrogenating with hydrogen gas in the presence of catalyst, e.g. palladium catalyst, in suitable solvent, e.g. ethyl acetate, to obtain the compound of formula (V).

The invention is further illustrated by the following non-limiting examples.

Example 1. Preparation of 1-Bromo-3,5-dinitrobenzene (VII)

To an inerted (N$_2$) flask was added concentrated sulfuric acid (500 mL) followed by 1,3-dinitrobenzene (100 g, 1 equivalent). The mass was stirred until complete dissolution. The mass was cooled to 15±5° C. and acetic acid (200 mL) was added. The mass was further cooled to 0±5° C. 1,3-Dibromo-5,5-dimethylhydantoin (130.9 g, 0.77 equivalents) was added in five equal parts at 15 min intervals. The mass was stirred for 1 h and then warmed to 25±5° C. over several hours followed by stirring for 24 h.

To another flask was added water (1 L) which was cooled to 5±5° C. The reaction mass was added to the cold water over 1-2 h while maintaining the temperature <20° C. The resulting slurry was stirred for 1 h at 25±5° C. The product was collected by filtration and washed with water (500 mL).

A flask at 25±5° C. was charged with water (1 L) followed by sodium bicarbonate (100 g) and stirred until complete dissolution. The wet cake obtained above was charged into the bicarbonate solution. The mass was stirred for 30-40 min. The product was collected by filtration and washed with water (500 mL).

The wet cake was charged back into a flask together with water (1 L). The mass was heated to 50±5° C. and stirred for 1 h. The material was filtered, washed with water (500 mL) and dried in a vacuum oven at 45±5° C. to give 135 g (91.9%) of yellow crystalline material at 99.4 HPLC a-% purity.

Example 2. Preparation of 2,4-Difluoro-3',5'-dinitro-1,1'-biphenyl (VI)

To an inerted (N$_2$) flask was charged acetonitrile (600 mL), water (10 mL) and triethylamine (169.5 mL, 3 equivalents). I-Bromo-3,5-dinitrobenzene (VII) (100 g, equivalent) was added and the mass was heated to 70±5° C. under nitrogen atmosphere. The solution was stirred for 30 min prior to cooling to 15±5° C. 2,4-Difluorophenylboronic acid (76.7 g, 1.2 equivalents) was added followed by palladium (II) acetate (1.28 g, 0.0047 equivalents). The mixture was heated to reflux (80-85° C.) over 2 h and maintained for 5-6 h. The mass was cooled to 25±5° C. followed by addition of diethanolamine (68.1 g, 1.6 equivalents) and water (550 mL). The mass was stirred for 1 h after which the solids were collected by filtration and washed with water (210 mL). The crude product was dried in a vacuum oven for 6 h at 45±5° C.

An inerted flask was charged with acetonitrile (210 mL) and the crude product. The mass was heated to reflux (85±5° C.) and stirred for 30 min. The mass was cooled over 3 h to 25±5° C. and stirred for an additional hour. The mass was filtered and washed with hexane (100 mL). The material was dried in a vacuum oven at 45±5° C. to give 86.0 g (75.8%) of pale yellow to brown crystalline material at 98.5 HPLC a-% purity.

Example 3. Preparation of 2',4'-Difluoro-[1,1'-biphenyl]-3,5-diamine (V)

Ethyl acetate (1000 mL), 2,4-Difluoro-3',5'-dinitro-1,1'-biphenyl (VI) (100 g, 1 equivalent) and Pd/C (5 g, 10% Pd on carbon, 50% water wet) were charged into an inerted (N$_2$) autoclave. The system was flushed with nitrogen several times prior introducing hydrogen (5 bar). The reaction mass was heated to 40-45° C. and stirred for 5-7 h. After completion of the reaction the system was thoroughly flushed with nitrogen and the system was cooled to 25±5° C. The catalyst was filtered off and washed with ethyl acetate (250 mL). The filtrate was washed with water (2×700 mL). Activated charcoal (5 g, 5 w-%) was added and the mixture was stirred for 1 h. The charcoal was filtered off and washed with ethyl acetate (250 mL). Ethyl acetate was distilled off under vacuum (T<45° C.). Toluene (200 mL) was added and distilled off under vacuum (T<45° C.). Toluene (200 mL) was added and the mixture was heated to 40±5° C. The mass was stirred for 10 min prior to cooling to 25±5° C. over 2 h. The product was collected by filtration and washed with toluene (100 mL). The product was dried in a vacuum oven at 45±5° C. to give 70.0 g (89.0%) of yellow crystalline material.

Example 4. Preparation of N3-(4-bromo-2-nitrophenyl)-2',4'-difluoro-[1,1'-biphenyl]-3,5-diamine (IV)

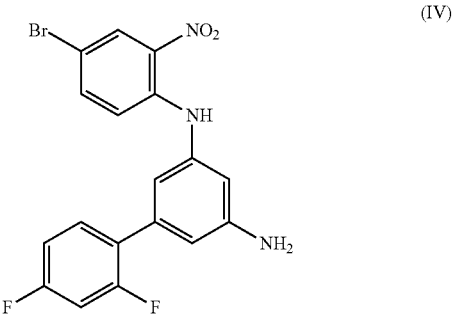 [SMILES: Nc1cc(Nc2ccc(Br)cc2[N+](=O)[O-])cc(-c2ccc(F)cc2F)c1]
(IV)

A flask inerted with N₂ was charged with dimethyl sulfoxide (250 mL) followed by 2',4'-difluoro-[1,1'-biphenyl]-3,5-diamine (V) (50 g, 1.0 equivalent). Then N,N-diisopropylethylamine (9.79 mL, 0.3 equivalents), ethoxytrimethylsilane (38.7 mL, 1.1 equivalents) and finally 4-bromo-2-fluoronitrobenzene (1.0 equivalent) were subsequently added. The bath temperature was adjusted to 100° C. (batch temperature 96-99° C.) and the dark red solution was stirred for 5 h. The contents were cooled to 60±5° C. after which methanol (250 mL) was added. Water (250 mL) was added over 40 min while keeping the batch temperature at 60±5° C. Then the mass was cooled to 20±5° C. over 1 h and then further stirred at that temperature for 2-3 h. The product was collected by filtration. The cake was washed with water (200 mL) followed by methanol (200 mL). The product was dried in a vacuum oven at 60° C. to give 86.2 g (92.5%) of brick red solid at 93.9 HPLC a-% purity.

Example 5. Purification of N3-(4-bromo-2-nitrophenyl)-2',4'-difluoro-[1,1'-biphenyl]-3,5-diamine (IV) by forming a mesylate salt intermediate (IVb)

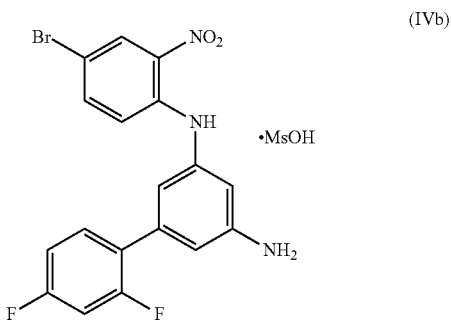 [SMILES: "·MsOH" ; Nc1cc(Nc2ccc(Br)cc2[N+](=O)[O-])cc(-c2ccc(F)cc2F)c1]

(IVb)

A flask inerted with N₂ was charged with toluene (860 mL) and 2-butanone (430 mL) followed by N3-(4-bromo-2-nitrophenyl)-2',4'-difluoro-[1,1'-biphenyl]-3,5-diamine (IV) (87.4 g, 1.0 equivalent). The mixture was heated to 75±5° C. and stirred until complete dissolution. Methanesulfonic acid (14.86 mL, 1.1 equivalents) was added over 17 min. The resulting orange slurry was stirred for 40 min followed by cooling to 60±5° C. After stirring for 60 min, the N3-(4-bromo-2-nitrophenyl)-2',4'-difluoro-[1,1'-biphenyl]-3,5-diamine mesylate salt (IVb) was collected by filtration and washed with toluene (160 mL).

The wet cake of mesylate salt (IVb) was charged into an inerted flask together with 2-propanol (570 mL) and toluene (285 mL). The thick slurry was heated to 75±5° C. Then triethylamine (31.9 mL, 1.1 equivalents) was added over 30 min. The now bright red mass was allowed to cool to 20±5° C. over night. The product was collected by filtration and the cake was washed two times with ice-cold 2-propanol (85 mL). The product was dried in an vacuum oven at 60° C. to give 75.4 g (86.3%) of N3-(4-bromo-2-nitrophenyl)-2',4'-difluoro-[1,1'-biphenyl]-3,5-diamine (IV) of 99.95 HPLC a-% purity.

Example 6. Preparation of N-(5-((4-bromo-2-nitrophenyl)amino)-2',4'-difluoro-[1,1'-biphenyl]-3-yl)cyclopropanesulfonamide (III)

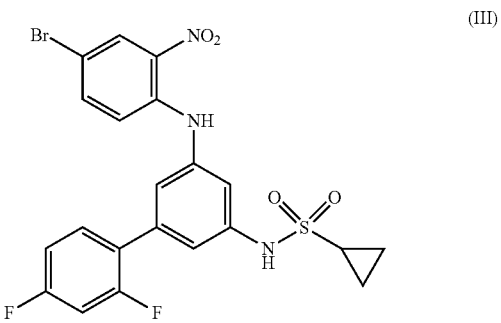 [SMILES: O=[N+]([O-])c1cc(Br)ccc1Nc1cc(NS(=O)(=O)C2CC2)cc(-c2ccc(F)cc2F)c1]

(III)

To a flask inerted with N₂ was added dry pyridine (110 mL) followed by N3-(4-bromo-2-nitrophenyl)-2',4'-difluoro-[1,1'-biphenyl]-3,5-diamine (IV) (36.4 g). The red slurry was cooled to 10±2° C. after which cyclopropanesulfonyl chloride (9.71 mL, 1.1 equivalents) was added over 10 min. After the addition the mixture was stirred for 1 h followed by further 1 h stirring at 20±5° C. To the now dark red solution was added water (7.80 mL, 5 equivalents) and the resulting mixture was stirred for 30 min.

To another flask was prepared a solution comprising of AcOH (127 mL), 2-propanol (110 mL) and water (145 mL). The solution was heated to 45±5° C. and seed crystals of N-(5-((4-bromo-2-nitrophenyl)amino)-2',4'-difluoro-[1,1'-biphenyl]-3-yl)cyclopropanesulfonamide (III) were added. The reaction mass was slowly added to this mixture while maintaining a temperature of 45±5° C. The mass was then heated to 70±5° C. and stirred for 1 h prior to cooling to 20±5° C. The product was collected by filtration and washed with 2×100 mL of water and 45 mL of ice-cold 2-propanol. The product was dried in a vacuum oven at 60° C. to give 42.9 g (94.5%) of orange crystalline solid at 98.4 HPLC a-% purity.

Example 7. Preparation of N-(5-((4-bromo-2-nitrophenyl)amino)-2',4'-difluoro-[1,1'-biphenyl]-3-yl)cyclopropanesulfonamide (III) (Alternate Method)

To a 1 L reactor inerted with nitrogen was charged ethyl acetate (210 mL), pyridine (67.1 mL, 5 equivalents) and N3-(4-bromo-2-nitrophenyl)-2',4'-difluoro-[1,1'-biphenyl]-3,5-diamine (IV) (70 g, 1 equivalent). To this thick mass was added cyclopropanesulfonyl chloride (20.37 mL, 1.2 equivalents) over 10 min. The resulting mixture was heated to 60±2.5° C. After reaction completion (about 4 h) acetic acid (glacial, 66.8 mL, 7 equivalents) was added followed by ethanol (420 mL). Water (175 mL) was added slowly while keeping the temperature at 60±5° C. The solution was seeded and then cooled to 40° C. over 2 h. The resulting mass was cooled to 0° C. over 3 h and stirred for 30 min before filtration. The cake was washed with water (210 mL) and ethanol (210 mL). After drying under vacuum (60° C.) 78.2 g of bright orange crystalline solid was obtained at 99.8 HPLC a-% purity.

Example 8. Preparation of 2',4'-difluoro-N3-(4-(1-methyl-1H-pyrazol-4-yl)-2-nitrophenyl)-[1,1'-biphenyl]-3,5-diamine (IIIb)

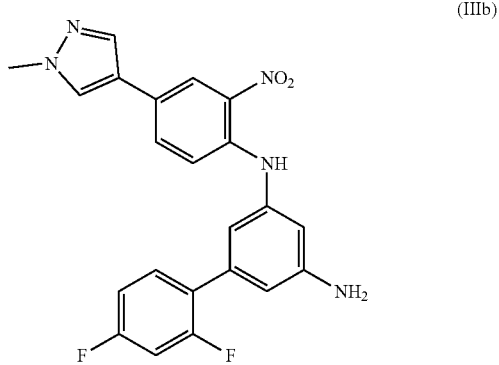 [SMILES: Cn1cc(-c2ccc(Nc3cc(N)cc(-c4ccc(F)cc4F)c3)c([N+](=O)[O-])c2)cn1]

(IIIb)

To a flask inerted with N2 was added dimethylsulfoxide (140 mL) and water (40 mL). To this solution was added N3-(4-bromo-2-nitrophenyl)-2',4'-difluoro-[11'-biphenyl]-3,5-diamine (IV) (20.0 g, 1 equivalent) followed by potassium carbonate (8.55 g, 1.3 equivalents), 1-methyl-4-(4,4,5,5-tetramethyl-1,3,2-dioxaborolan-2-yl)-1H-pyrazole (12.38 g, 1.25 equivalents) and activated charcoal (2 g, CN1). The resulting mixture was degassed by adjusting the pressure to 100 mbar for a few minutes and back filling the flask with nitrogen. The procedure was repeated twice. Finally palladium (II) acetate (0.08 g, 0.0075 equivalents) and triphenylphosphine (0.281 g, 0.0225 equivalents) were added and the mixture was heated to 100±5° C. over 4 h. After reaching the 100±5° C. the mixture was cooled back to 80±5° C. and ethanol (60 mL) was added. The mass was filtered and the cake was washed with ethanol (20 mL).

The temperature of the filtrate was adjusted to 80±5° C. and water (80 mL) was added over 30 min. The mass was allowed to stir for 30 min and then allowed to cool to 20±5° C. The product was isolated by filtration and the cake was washed with water (40 mL) and ethanol (40 mL). The product was dried in a vacuum oven at 60° C. to give 20.55 g of red solid at 99.9 HPLC a-% purity.

Example 9. Preparation of N-(2',4'-difluoro-5-((4-(1-methyl-1H-pyrazol-4-yl)-2-nitrophenyl)amino)-[1,1'-biphenyl]-3-yl)cyclopropanesulfonamide (II) from Compound (III)

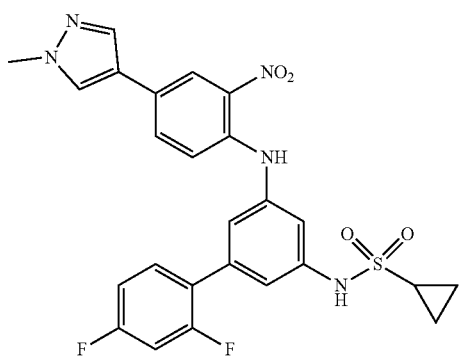

(II)

To a flask inerted with N2 was added dimethylsulfoxide (600 mL) and water (170 mL). To this solution was added N-(5-((4-bromo-2-nitrophenyl)amino)-2',4'-difluoro-[1,1'-biphenyl]-3-yl)cyclopropanesulfonamide) (III) (85.0 g, 1 equivalent) followed by potassium carbonate (29.1 g, 1.3 equivalents), 1-methyl-4-(4,4,5,5-tetramethyl-1,3,2-dioxaborolan-2-yl)-1H-pyrazole (42.2 g, 1.25 equivalents) and activated charcoal (8.5 g, Norit CN1 or SX Ultra). The resulting mixture was degassed by adjusting the pressure to 100 mbar for a few minutes and back filling the flask with nitrogen. The procedure was repeated twice. Finally palladium (II) acetate (0.27 g, 0.0075 equivalents) and triphenylphosphine (0.96 g, 0.0225 equivalents) were added and the mixture was heated to 100±5° C. over 4 h. After reaching the 100±5° C. the mixture was cooled back to 80±5° C. and ethanol (255 mL) was added. The mass was filtered and the cake was washed with ethanol (85 mL). The temperature of the filtrate was adjusted to 60±5° C. and water (467 mL) was added over 1 h. The mass was allowed to stir for 1 h and then cooled 10° C./min to 5±5° C. The product was isolated by filtration and the cake was washed with water (2×60 mL) and ethanol (2×85 mL). The product was dried in a vacuum oven at 60° C. to give 76.9 g (90.2%) of red solid at 98.3 HPLC a-% purity.

Example 10. Preparation of N-(2',4'-difluoro-5-((4-(1-methyl-1H-pyrazol-4-yl)-2-nitrophenyl)amino)-[1,1'-biphenyl]-3-yl)cyclopropanesulfonamide (II) from Compound (IIIb)

An interted flask was charged with pyridine (20 mL) and 2',4'-difluoro-N3-(4-(1-methyl-1H-pyrazol-4-yl)-2-nitrophenyl)-[1,1'-biphenyl]-3,5-diamine (IIIb) (5 g, 1 equivalent). The gelatinous mass was diluted with 20 mL of pyridine. Cyclopropane-sulfonyl chloride (1.33 mL, 1.1 equivalents) was added to the mixture over 1 min. After 1 h another 1.33 mL of cyclopropanesulfonyl chloride was added. After 1 h of further stirring water (1.07 mL, 5 equivalents) was added and the mass was stirred for 15 min. Acetic acid (20 mL) was added and the mixture was heated to 45±5° C. 2-Propanol (20 mL) was added followed by water (20 mL). The mass was allowed to 5 cool to 20±5° C. Product was collected by filtration and washed with water (2×20 mL) and 2-propanol (20 mL). The product was dried in a vacuum oven at 60° C. to give N-(2',4'-difluoro-5-((4-(1-methyl-1H-pyrazol-4-yl)-2-nitrophenyl)amino)-[1,1'-biphenyl]-3-yl)cyclopropanesulfonamide (II) (5.65 g, 90.6%) at 99.2 a-% purity.

Example 11. Preparation of N-(2',4'-difluoro-5-(5-(1-methyl-1H-pyrazol-4-yl)-1H-benzo[d]imidazol-1-yl)-[1,1'-biphenyl]-3-yl)cyclopropanesulfonamide (1A)

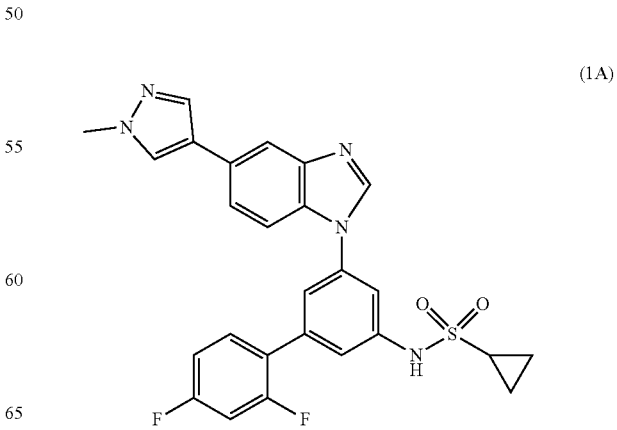

(1A)

A reactor was inerted with nitrogen and charged with formic acid (280 mL), N-(2',4'-difluoro-5-((4-(1-methyl-1H-pyrazol-4-yl)-2-nitrophenyl)amino)-[1,1'-biphenyl]-3-yl)cyclopropanesulfonamide (40 g) and 5% palladium on charcoal (4.86 g, 50% water-wet, 0.015 equivalents Pd). Hydrogen was introduced (2 bar) after thorough flushing with nitrogen and the reactor contents were heated to 30±2° C. The dark red slurry dissolved completely as the reaction progressed. The reaction was stopped by replacing the hydrogen with nitrogen when the liquid turned from red to colorless (4 h). The catalyst was filtered off and the filtrate was heated to 100±5° C. for 1 h.

120 mL of formic acid was distilled off under reduced pressure (100 mbar, 46° C.). 2-Propanol (106 mL) was added and the solution was heated to 80±5° C. Water (240 mL) was added while keeping the temperature >70° C. The solution was seeded and the mixture was cooled first at 5° C./h to 50° C. and then 10° C./h to 20° C. The mass was further cooled to 0±5° C. over 2 h and then the product was collected by filtration. The cake was washed with 2-propanol (50 mL) and dried at 60° C. in a vacuum oven. The yield was 37.4 g (89.0%) of light beige colored crystalline solid at 99.51 HPLC a-% purity. The obtained compound (IA) was in the form of 1:1 solvate with formic acid.

The formic acid was removed from the 1:1 formic acid solvate (12.3 g) by 5 adding it into a flask together with 2-butanone (98.4 mL). The mixture was heated to 75° C. and stirred for 2 h. The mass was allowed to cool to RT after which it was filtered and washed with 2-butanone (12.3 mL). The product was dried in a vacuum oven at 60° C. to give 10.62 g (94.2%) of compound (1A) as an off-white powder. The compound was free of formic acid by $^1$H-NMR.

The invention claimed is:

1. A compound chosen from:

formula (V):

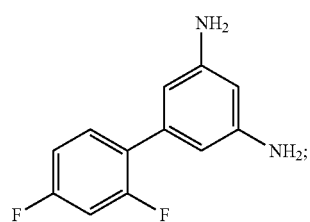

formula (IV):

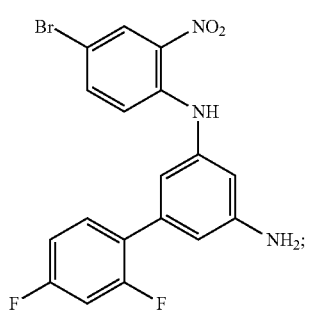

formula (III):

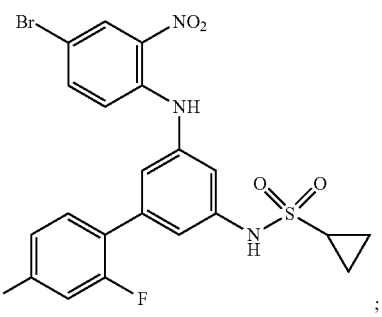

formula (IIIb):

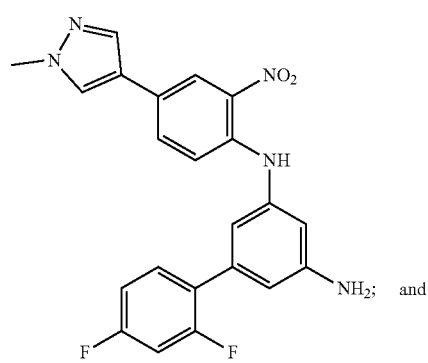

and formula (II):

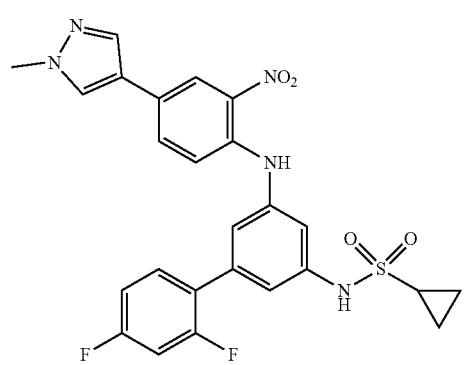

.

2. A process for the preparation of a compound of formula (IV)

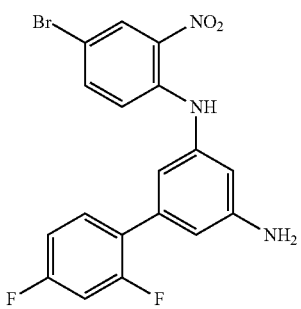

comprising the steps of:
a) reacting 2',4'-difluoro-[1,1'-biphenyl]-3,5-diamine of formula (V)

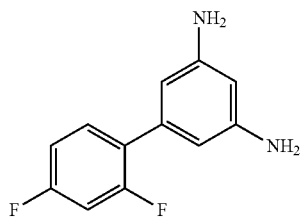

(V)

with 4-bromo-2-fluoronitrobenzene in the presence of an organic base and an organosilane to obtain a compound of formula (IV)

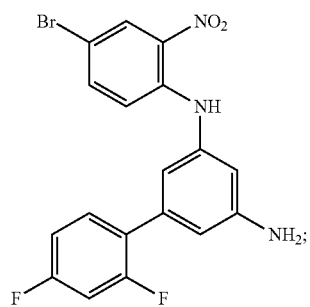

(IV)

b) treating the product obtained from step (a) with an organic acid and isolating the formed organic salt;

c) releasing the compound of formula (IV) from its salt form.

3. The process according to claim 2, wherein the organic base used in step a) is N,N-diisopropylethylamine (DIPEA).

4. The process according to claim 2, wherein the organosilane used in step a) is ethoxytrimethylsilane.

5. The process according to claim 2, wherein the organic acid used in step b) is a sulfonic acid.

6. The process according to claim 5, wherein the sulfonic acid is methanesulfonic acid, p-toluenesulfonic acid, o-toluenesulfonic acid, ethanesulfonic acid or benzenesulfonic acid.

7. The process according to claim 6, wherein the sulfonic acid is methanesulfonic acid or p-toluenesulfonic acid.

8. The process according to claim 7, wherein the sulfonic acid is methanesulfonic acid.

9. The process according to claim 2, wherein step c) is carried out by heating the salt in an organic solvent in the presence of an organic base.

* * * * *